US 9,964,556 B2

(12) United States Patent
Wenczel et al.

(10) Patent No.: US 9,964,556 B2
(45) Date of Patent: May 8, 2018

(54) MICROPLATE READER WITH INCUBATION DEVICE (71) Applicant: TECAN TRADING AG, Männedorf (CH)

(72) Inventors: Gyoergy Wenczel, Seekirchen (AT); Harald Gebetsroither, Grödig (AT); Friedrich Menges, Berchtesg (AT)

(73) Assignee: TECAN TRADING AG, Mannedorf (CH)

( * ) Notice: Subject to any disclaimer, the term of this patent is extended or adjusted under 35 U.S.C. 154(b) by 185 days.

(21) Appl. No.: 14/654,382

(22) PCT Filed: Oct. 30, 2014

(86) PCT No.: PCT/EP2014/073389
§ 371 (c)(1),
(2) Date: Jun. 19, 2015

(87) PCT Pub. No.: WO2015/067529
PCT Pub. Date: May 14, 2015

(65) Prior Publication Data
US 2016/0003859 A1    Jan. 7, 2016

(30) Foreign Application Priority Data

Nov. 7, 2013  (CH) ...................... 1867/13

(51) Int. Cl.
G01N 35/02   (2006.01)
C12M 1/34    (2006.01)
(Continued)

(52) U.S. Cl.
CPC ............ G01N 35/028 (2013.01); B01L 9/523 (2013.01); C12M 23/12 (2013.01); C12M 23/38 (2013.01);
(Continued)

(58) Field of Classification Search
CPC ................. G01N 35/028; G01N 35/04; G01N 2035/00356; G01N 2035/0477;
(Continued)

(56) References Cited

U.S. PATENT DOCUMENTS 6,097,025 A      8/2000  Modlin
2014/0045210 A1*  2/2014  Menges ............. G01N 21/6428
435/34

FOREIGN PATENT DOCUMENTS

EP    1623759 A1    2/2006
WO    96/21855 A1   7/1996
(Continued)

OTHER PUBLICATIONS

International Search Report for PCT/EP2014/073389 filed Oct. 30, 2014.
(Continued)

Primary Examiner — Michael L Hobbs
(74) Attorney, Agent, or Firm — Notaro, Michalos & Zaccaria P.C.

(57) ABSTRACT

Microplate reader has measuring space, action source, measuring device for biological structure signals of microplate wells, transport support for positioning wells in relation to an optical axis of the device and controller for the action source, the measuring device and the transport support. An incubation apparatus with a frame accommodates a microplate with wells having bottoms for reducing liquid evaporation. The frame has a first opening surrounded by an inner wall for the microplate and an outer wall parallel to the inner wall and connected thereto by an intermediate bottom so that a channel is formed and the intermediate bottom for accommodating a liquid adjusted to the content of the microplate wells. The incubation apparatus has a support surface with a second opening for a microplate and, as a
(Continued)

result, at least a portion of the well bottoms is freely accessible by the second opening.

18 Claims, 3 Drawing Sheets

(51) Int. Cl.
    *B01L 9/00*         (2006.01)
    *C12M 1/32*        (2006.01)
    *C12M 1/00*        (2006.01)
    *G01N 35/04*       (2006.01)
    *G01N 35/00*       (2006.01)

(52) U.S. Cl.
    CPC ........ *G01N 35/04* (2013.01); *B01L 2200/142* (2013.01); *B01L 2300/041* (2013.01); *B01L 2300/0829* (2013.01); *G01N 2035/00356* (2013.01); *G01N 2035/0403* (2013.01); *G01N 2035/0477* (2013.01)

(58) Field of Classification Search
    CPC . G01N 2035/0403; G01N 2035/00287; G01N 2035/0405; G01N 21/6428; C12M 23/12; C12M 23/38; B01L 9/523; B01L 2300/041; B01L 2300/0829; B01L 2200/142; Y10S 436/807
See application file for complete search history.

(56) References Cited

FOREIGN PATENT DOCUMENTS

WO     02/024336 A1     3/2002
WO     03/089137 A1    10/2003

OTHER PUBLICATIONS

International Preliminary Patent Report and Written Opinion for PCT/EP2014/073389 filed Oct. 30, 2014.

\* cited by examiner

MICROPLATE READER WITH INCUBATION DEVICE

BACKGROUND OF THE INVENTION

Field of the Invention

The invention relates to a microplate reader with an incubation apparatus for reducing liquid evaporation from wells of microplates.

Microplate readers, with which the contents of one or more wells of a microplate can be assayed or analyzed in an optical manner, have been known for some time. All multiwell plates which have a plurality of wells or containers arranged in an array are referred to as microplates in conjunction with the present invention. Especially preferred microplates have at least approximately the mass and the footprint of a microplate according to the SBS standard, as was published by the American National Standards Institute (ANSI). Standard microplates with wells that are equipped with a round bottom, flat bottom, or V-shaped bottom are known for example. All of these standard microplates having greatly varying well shapes share the feature that the axial spacing of the respective wells arranged in an array is also standardized (compare ANSI_SBS 1-2-3-4-2004 standard for microplate dimensions from the year 2006). This axial spacing is, for example, in 24 well (4×6) plates 18 mm, in 96-well (8×12) plates 9 mm, in 384 well (16×24) plates 4.5 mm, and in 1536 well (32×48) plates 2.25 mm. The height of a standard microplate can vary greatly depending on the type and is typically between 10.4 mm (for example, 1536 V base deep well plate) and 44 mm (for example, 96 well Masterblock® from Greiner).

Known microplate readers are equipped with the appropriate light sources and/or detectors to assay samples in the wells of microplates on the basis of their absorption, and/or fluorescence and/or luminescence. The samples are typically located in a liquid which is subjected to the influences of the surroundings. In particular in the case of long-lasting experimental series, which are typically carried out in microplate readers, which are stationary per se, during hours or even days and possibly also at temperatures elevated in relation to the room temperature, evaporation problems can result for the liquid-containing samples. The evaporation of the sample liquid results in thickening and therefore in a change of the concentration of buffer substances and molecules to be assayed (analytes). Thus, for example, the growth conditions for cell-based experiments or the reaction of cells to experimentally induced influences are changed. In addition, it has been observed that the sample liquid of wells arranged in the corners of a standard microplate is subjected to significantly more evaporation problems than of wells arranged in the middle of a microplate. In turn, this means that the thickening does not occur in a homogeneously distributed manner over all wells of a microplate, but rather results in differences, and therefore in non-comparable results, within the same test series.

Description of Related Art

Apparatuses for preventing or at least reducing such evaporation problems are known from the prior art. Thus, U.S. Pat. No. 5,789,251 discloses a self-adhesive cover film, which can be pierced using a pipette tip, for sealing the wells of the standard microplate; however, such a cover film can impair the optical analysis of the experimental results in the microplate reader, so that this film must be implemented as highly transparent and cannot have condensation products on its inner surface. Otherwise, the film must be removed for the optical analysis, which at worst can result in spilling or other changes of the samples (for example, by cross-contamination). A very complex applicator is known from U.S. Pat. No. 6,408,595 B1, using which self-adhesive cover films can be applied to standard microplates.

Storing a standard microplate in a climate-controlled chamber having an installed liquid reservoir and thus preventing the occurrence of evaporation problems is known from U.S. Pat. No. 6,518,059 B1; however, the microplate must be removed from the climate chamber after the incubation time and transferred for the optical analysis to a microplate reader. Evaporation problems can also occur during this transfer and also during the time in the microplate reader. US 2006/0023299 A1 also discloses a climate-controlled chamber, which is arranged inside an incubator box, which can be covered and is shielded against magnetic fields. In place of the climate-controlled chamber, a microplate can be laid in the incubator box, which is equipped with double circumferential walls. A bath having sterilized water is arranged between the two walls of the incubator box, using which nearly 100% saturation of the culture gas with water can be achieved in the incubator box. In contrast, the patent application US 2008/0180793 A1 discloses a system having a microplate inserted in a living cell chamber, the wells of which are supplied with moist culture gas, which is enriched in a special conditioning facility of the system with water vapor, via a gas line system.

The use of cover apparatuses for microplates is also known for preventing evaporation problems. Patent EP 0 311 440 B1 discloses an apparatus for carrying out liquid reactions, in which a microplate is clamped between two heating plates. In this case, temperatures between 37° C. and 90° C. can be set, wherein the wells of the microplate are covered with an elastic plate of the upper heating plate to reduce the evaporation of the liquid in the wells. Patent EP 1 623 759 B1 discloses a system having a specially constructed microplate/cover combination, wherein the enclosure walls of the microplate and the cover are implemented so that they interlock and thus seal the space above the wells. The use of standard microplates is not possible in this system.

U.S. Pat. No. 7,767,154 B2 discloses a somewhat different approach, in which a cover having catch pins is pressed onto a microplate so that these catch pins are held with friction lock in corresponding catch openings of the microplate. A circumferential seal on the cover additionally reduces the possibility that vapors originating from the wells can escape into the surroundings. However, a special embodiment of the microplate and the cover is necessary and the closing and opening of the microplate/cover combination must be performed using a special and quite complicated tool. The use of standard microplates is also not possible here.

Still another approach is known from EP 1 465 730 B1. A cover is laid on the wells of a multiwell plate therein so that the cover touches the sample liquid over the entire surface, wherein sample liquid escaping from overfilled wells is used as a seal. The risk thus exists that molecules to be analyzed will be lost. The use of standard microplates is also not possible in this system.

The document WO 02/24336 A1 discloses an incubation apparatus with a cover and a retaining frame, in which one or several titer plates can be inserted. The cover is pressed onto the seals and the retaining frame and a stamp seals a continuous recess of the retaining frame beneath the titer plate, so that the titer plate is always sealingly enclosed.

The document WO 03/089137 A1 discloses a system, a substrate plate (microplate) and an incubation apparatus for carrying out biological tests. Each well base of the microplate comprises a micro-array substrate with aligned flow channels and the incubation apparatus comprises an incubation chamber for retaining the microplate in a heating block and a cover for sealing the incubation chamber. The cover comprises a seal whose openings are arranged in an array in such a way that when the cover is inserted each well of the microplate is sealed individually.

Disadvantages existing in the prior art comprise the fact that an injector for adding reagents cannot be used without the film having to be removed from the microplate or the cover having to be lifted off before laying the microplate in a microplate reader (U.S. Pat. No. 5,789,251 represents a possible exception). The more completely the seal of the wells against the surroundings is implemented, the less is the possible gas exchange (which is important for cell cultures, for example) in the case of cell-based experiments. Loosely covered microplates nonetheless experience a possibly reduced, but still existing thickening of the sample liquid due to evaporation. Condensation products which accumulate on the underside of optically transparent cover films or microplate covers result in incorrect measurements in the absorbance mode. Cover films or covers on microplates prevent fluorescence measurements in the top detection mode; luminescence measurements are not possible through microplate covers.

SUMMARY OF THE INVENTION

It is therefore an object of the present invention to propose a microplate reader with which the disadvantages known from the prior art can be substantially eliminated.

This object is achieved by a microplate reader and an incubation apparatus as defined in claim 1. The microplate reader in accordance with the invention comprises at least:
  a) a measuring space;
  b) an action source which is configured for producing an interaction with biological structures in wells of a microplate and for effecting or generating a measurable signal;
  c) a measuring device which is configured for detecting a signal which is emitted by biological structures in wells of a microplate or which was effected or generated by the action source in or on biological structures in wells of a microplate, wherein the measuring device defines an optical axis;
  d) a transport support which can be extended at least partly out of the measuring space and which is configured for positioning wells of a microplate in relation to the optical axis of the measuring device of the microplate reader, in that the transport support is configured to be movable in at least one direction within the measuring space, and
  e) a controller which is configured for controlling the action source, the measuring device and the movements of the transport support of the microplate reader.

The microplate reader in accordance with the invention is characterized in that it comprises an incubation apparatus for reducing liquid evaporation from wells of a microplate reader, wherein:
  (i) the incubation apparatus comprises a frame for accommodating a microplate with wells having well bottoms;
  (ii) the frame comprises a first opening surrounding an inner wall, the dimensions of which is configured for inserting a microplate, and
  (iii) the frame comprises an outer wall which extends substantially parallel to the inner wall, and which is connected to the inner wall via an intermediate bottom, so that a channel surrounding the first opening is formed by the two walls and the intermediate bottom for accommodating a liquid adjusted to the content of the microplate wells.

The microplate reader in accordance with the invention is further characterized in that the incubation apparatus comprises a support surface with a second opening, wherein said that support surface is arranged on the inner wall and is configured for supporting an inserted microplate, and wherein—as a result of the second opening—at least a portion of the bottoms of the wells of a microplate inserted into the incubation apparatus is freely accessible through the second opening.

Further preferred and inventive features of the microplate reader, an incubation frame and an incubation cassette and their use are provided in the respective dependent claims.

Advantages of the incubation cassette according to the invention and the microplate reader according to the invention comprise the following:
  The incubation frame and the incubation cassette are dimensioned and configured so that they can be inserted easily (manually or by robot) into the transport support of a microplate reader and also can be removed easily (manually or by robot) again from said transport support.
  The fixing of the microplate in a defined position on the transport support of the microplate reader and/or in the incubation frame or in the frame of the incubation cassette is caused by a proven clamping mechanism.
  At least a part of the bottoms—but preferably all bottoms of the wells—of a microplate inserted into the incubation frame or into the incubation cassette remain freely accessible from below, i.e. through the integration frame or the frame of the incubation cassette and through the reading opening of the transport support, so that the bottom reading mode, which is known per se, of the microplate reader can be applied.
  The incubation frame or the incubation cassette provides a reservoir in the form of a channel that can be filled with liquid (for example, water), which encloses an inserted microplate and enriches the atmosphere in the immediate surroundings of the microplate wells accordingly.
  The channel can be filled or refilled at least partially with a liquid by means of a hand pipette, a pipette of a laboratory workstation, or also by means of an injector of the microplate reader.
  To shield the enriched atmosphere from the environment, a cover can be laid on the incubation frame, thus providing an incubation cassette; this cover can be lifted off and put on again by the microplate reader itself (see European patent application EP 13 178 313.6, published as EP 2 696 205 A1), so that the microplate wells are freely accessible for the time of all necessary actions.
  The evaporation rate of the liquid from the wells of a microplate which is inserted into the incubation cassette and covered is significantly reduced in relation to a conventional covered microplate without incubation cassette.

The gas exchange, which is required for cell cultures or for cell-based experiments, between the microplate wells and the surroundings can be assisted by means of sporadic lifting of the cover of the incubation cassette by the operating personnel, a robot, or by the microplate reader itself (compare European patent application 13 178 313.6, published as EP 2 696 205 A1).

If an incubation frame without cover is used in a respectively optimized microplate reader with small measuring space volume, the gas atmosphere in the measuring space is enriched accordingly by the liquid in the reservoir surrounding the inserted microplate.

Arbitrary microplates can be inserted into the incubation frame or incubation cassette, wherein standard microplates according to ANSI_SBS 1-2-3-4-2004 standard are preferred. The use of special microplates thus becomes superfluous for carrying out experiments using cell cultures or cell-based experiments.

Thanks to the use of an incubation frame or incubation cassette, long-term experiments can be carried out in a microplate reader even at elevated temperature (for example, at 37° C.).

In the course of multi-day cell culture experiments, in the case of the use of an incubation cassette when the cassette cover is temporarily raised, or the use of an incubation frame, further substances can be injected by using an injector into the wells of the microplate inserted into the incubation cassette, to trigger or stop reactions or to supply nutrients or other substances which influence the cell growth to the cell cultures.

An exemplary microplate reader with incubation frame or incubation cassette will be shown on the basis of schematic drawings. These drawings document selected embodiments of the subject matter of the invention, but shall not restrict the scope of the present invention, wherein:

BRIEF DESCRIPTION OF THE DRAWINGS

FIG. 5 shows vertical partial sections through a covered incubation cassette, wherein:

DETAILED DESCRIPTION OF THE INVENTION

Figure 1:
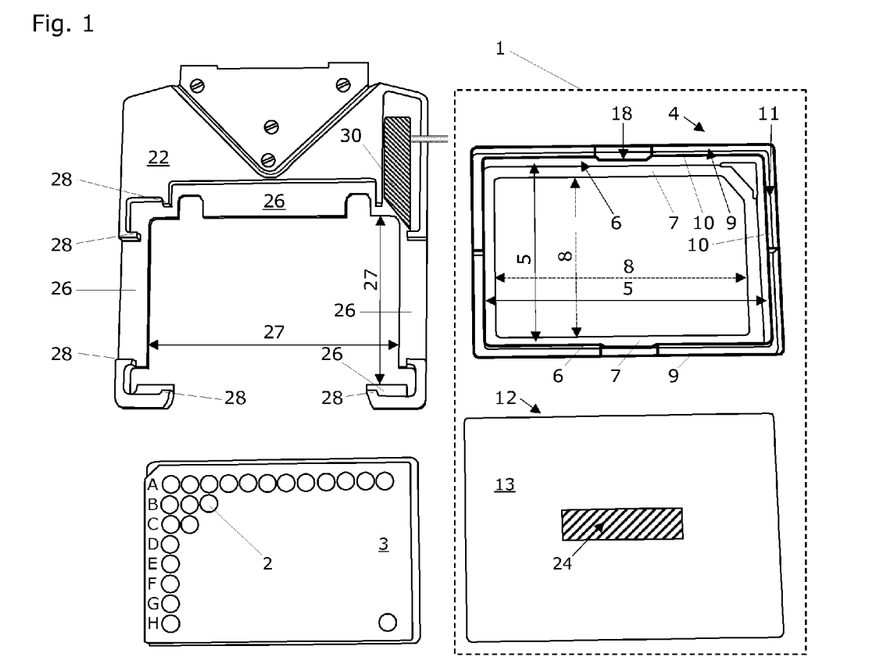
FIG. 1 shows a view of a transport support of a microplate reader for transporting an incubation cassette, an incubation frame or components of the incubation cassette, and a standard microplate according to ANSI_SBS 1-2-3-4-2004 standard.

FIG. 1 shows a view of components of the incubation apparatus in accordance with the invention in form of an incubation cassette 1, a transport support 22 of a microplate reader 23 for transporting an incubation cassette 1 and a standard microplate 3 according to the SBS standard as published by the American National Standards Institute (ANSI). The illustrated microplate 3 comprises 96 wells 2 which are arranged in an 8×12 array and comprise well bottoms which are not all shown. The 8 rows of 12 wells 2 each are designated with the letters A to H (cf. ANSI_SBS 1-2-3-4-2004; 2006).

Figure 5A:
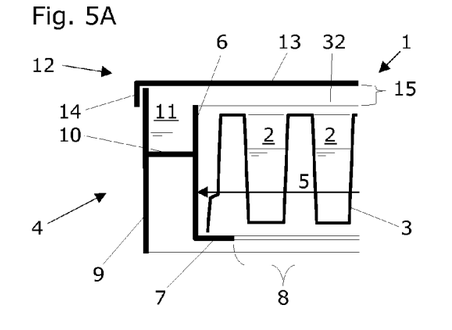
FIG. 5A shows a circumferential gap.

The incubation cassette 1 in accordance with the invention is formed for reducing the liquid evaporation from wells 2 of microplates 3 and preferably comprises a frame 4 and a cover 12 (see the region with the dashed border in FIG. 1). Alternatively, the frame 4 can be used as a cover-free incubation frame 4, i.e. without the cover 12 (see FIG. 6). The incubation cassette 1 for reducing the liquid evaporation from wells 2 of microplates 3 comprises a preferably substantially rectangular frame 4 for accommodating a microplate 3 (preferably a microplate according to the ANSI_SBS 1-2-3-4-2004 standard) with wells 2 containing liquid. The frame 4 or the incubation frame 4 comprises a central first opening 5, whose dimensions are configured for the complete insertion of a microplate 3. The central first opening 5 is surrounded by a preferably substantially perpendicular inner wall 6, wherein a preferably substantially horizontal support surface 7 with a central second opening 8 is preferably arranged at its bottom end. Said support surface 7 is configured for carrying an inserted microplate 3. The frame 4 of the incubation cassette 1 or the incubation frame 4 further comprises an outer wall 9 which preferably extends substantially parallel to the inner wall 6 and which is connected to the inner wall 6 by an intermediate bottom 10, so that a channel 11 which surrounds the central first opening 5 and is provided for accommodating a liquid adjusted to the content of the microplate wells 2 is formed by the two walls 6, 9 and the intermediate bottom 10. The cover 12 of the incubation cassette 1 is used for covering the frame 4 with inserted microplate 3 and comprises a substantially flat plate 13 and a downwardly protruding and circumferential edge 14 which is preferably integrally attached to said plate 13, or several downwardly protruding edge portions 34 (see FIG. 2). The cover 12 is configured for placement on the frame 4 in such a way that the plate 13 rests on an upper end of the outer wall 9 and said edge 14 or the edge portions 34 of the cover 12 engage downwardly beyond the outer wall 9 of the frame 4 (see FIGS. 2, 5A and 5B). Alternative cover arrangements are shown in FIGS. 5C and 5D.

The cover 12 preferably comprises an at least partly metalized, magnetizable surface 24, wherein said magnetizable surface 24 is selected from a group which comprises a self-adhesive metal foil, an extrusion-coated metal plate and a glued metal plate, and wherein the metal comprises iron, nickel and their alloys. The cover 12 is preferably made of a chemically inert synthetic material and is produced by means of injection molding for example. The cover 12 can comprise a seal which is sealingly applied to the outer wall 9 of the frame 4 in the region of its upper end (not shown). Similarly, or as an alternative thereto, the outer wall 9 of the frame 4 can comprise a seal in the region of its upper end which is sealingly applied to the cover 12 (not shown).

FIG. 1 further shows a transport support 22 of a microplate reader 23 (see FIGS. 2 and 6), wherein the transport support 22 comprises a support surface 26 for the support of a frame 4 of an incubation cassette 1 or an incubation frame 4 in accordance with the invention. If several microplates 3 are to be processed in parallel, it is preferable that the transport support 22 comprises two or more support surfaces 26 for supporting a respective frame 4 (i.e. two or more frames 4) of the incubation cassette 1 or incubation frame 4 in accordance with the invention. A transport support 22 can comprise (as shown in FIG. 1) several support surfaces 26 for placing only one incubation cassette 1 and incubation frame 4. The transport support 22 can preferably be moved within the housing 25 of the microplate reader 23 in at least one horizontal direction, e.g. in an X direction of a Cartesian system of coordinates (see FIG. 6), for the optical analysis of the samples in the wells 2 of a microplate 3 and/or for lifting/placing a cover 12 of or on the incubation cassette 1 and/or for adding substances to the wells 2 of the microplate 3 and/or to the channel 11 of the incubation cassette 1 or the incubation frame 4. The transport support 22 can further be moved in a horizontal direction into an open region of the microplate reader 23 or even beyond the microplate reader for placing or lifting an incubation cassette 1 or an incubation frame 4. The microplate reader is preferably configured for controlling and performing said movements of the transport support 22 and for releasing and/or pressing the spring bolt 30.

The support surface 26 of the transport support 22 preferably comprises a substantially rectangular reading opening 27, which is adjusted with respect to its size and position to the central second opening 8 of the frame 4 of the incubation cassette 1 or the incubation frame 4 in accordance with the invention. It is especially preferred that the support surface 26 comprises retaining webs 28 at the corners of the reading opening 27 (5 out of a total of 8 illustrated retaining webs are designated here with reference numeral 28), which are configured for engagement in respective retaining openings 29 in the inner wall 6 of the frame 4 of the incubation cassette 1 or the incubation frame 4 (marked in gray in FIG. 2). The transport support 22 preferably comprises a generally known spring bolt 30 for positioning and holding a microplate 3 inserted into the incubation cassette 1.

Figure 2:
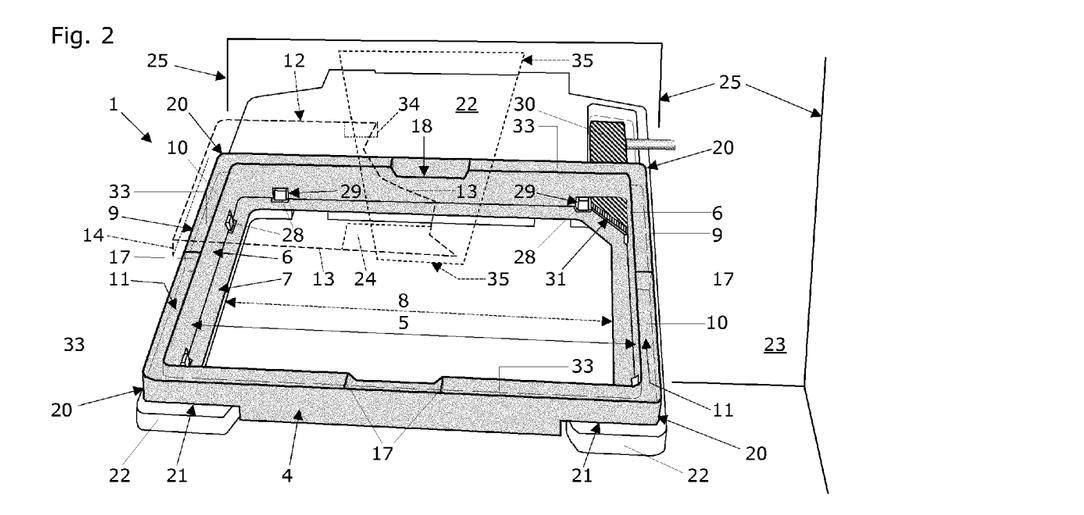
FIG. 2 shows a view of a frame of an incubation cassette or incubation frame, which lies with removed cover on a transport support of a microplate reader.

FIG. 2 shows a view of a frame 4 of an incubation cassette 1 or an incubation frame 4, which rests with removed cover 12 (therefore indicated by the dashed line here) on a transport support 22 of a microplate reader 23. Said cover 12 can comprise a circumferential edge 14 (see left side) or a number of edge portions 34 (see rear), wherein the edge portions 34 can be arranged to engage downwardly beyond the outer wall 9 in the region of the corners 20 of the frame 4. Edge portions 34 can be provided in addition or alternatively, which can be arranged between the corners 20 to engage downwardly beyond the outer wall 9. The circumferential edge 14 can exert a sealing function between the gas atmosphere 32 in the interior of the intubation set 1 (see FIG. 5A), in addition to the centric placement and for preventing the slippage of the cover 12 from the frame 4. The edge parts 34 can hardly exert such a sealing function. Alternative cover configurations and respective cover supports are shown in FIGS. 5C and 5D.

Figure 5B:
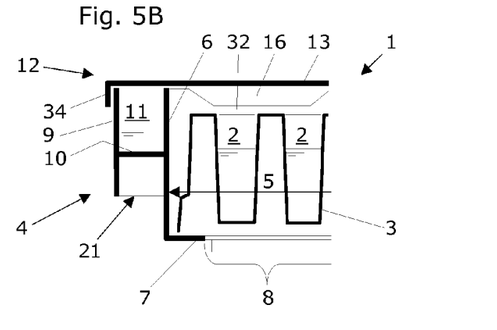
FIG. 5B shows one of multiple depressed regions as a connection between channel and first opening.
Figure 5C:
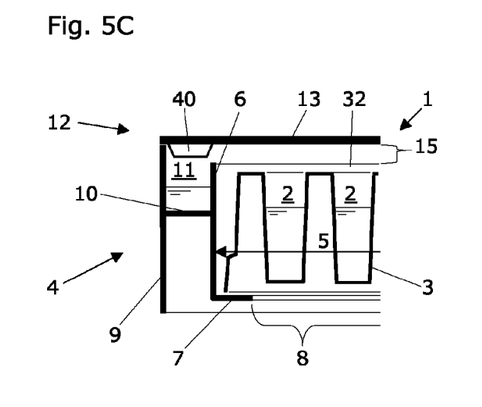
FIG. 5C shows a first alternative cover on a frame of an intubation cassette according to FIG. 5A.
Figure 5D:
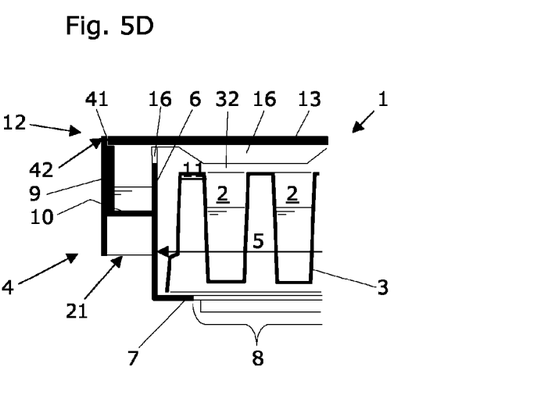
FIG. 5D shows a second alternative cover on an alternative frame with respect to FIG. 5B.

In the case of the incubation cassette 1 and the incubation frame 4 as are shown here, the inner wall 6 of the frame 4 reaches approximately up to the same height as the outer wall 9, but it is preferable in such a case that the inner wall 6 comprises depressed regions 16, so that when the cover 12 is placed each depressed region 16 connects the central first opening 5 to the channel 11 which surrounds the same (see FIGS. 5B and 5D). It can be alternatively provided that the inner wall 6 of the frame 4 does not reach up to the outer wall 9, so that when the cover 12 is placed a circumferential gap 15 connects the central first opening 5 to the channel 11 that surrounds the same (see FIGS. 5A and 5C). It can further be provided that (as shown in FIG. 2) the inner wall 6 of the frame 4 is connected via substantially perpendicular webs 17 to the outer wall 9 of the frame 4, by means of which the channel 11 or the reservoir 11 is subdivided to a number of channel sections 33.

It is preferred that the inner wall 6 of the frame 4 of an incubation cassette 1 or an incubation frame 4 comprises sections 18 (see FIGS. 1 and 2) which are configured for the engagement of fingers 19 of a microplate handling robot (shown in FIG. 3) or an operator (not shown) for transporting a microplate 3 (preferably a microplate 3 according to ANSI_SBS 1-2-3-4-2004 Standard). The frame 4 is preferably made from a chemically inert synthetic material and by means of injection molding for example.

The channel 11, which surrounds the central first opening 5, preferably comprises a water-binding material, which emits water vapor to a gas atmosphere situated above the wells 2 of the microplate 3 at temperatures of at least 35° C., preferably at least 25° C. (see FIGS. 5A and 5B). Swellable polyacrylate is especially preferred as a water-binding material (see below).

In order to achieve a secure fit on the transport support 22 of the microplate reader 23, the outer wall 9 of the frame 4 of the incubation cassette 1 or the incubation frame 4 comprises notches 21 on all corners 20, which notches are configured for placing the frame 4 with or without a microplate 3 (preferably according to the ANSI_SBS 1-2-3-4-2004 standard) inserted into said frame 4 or incubation frame 4, on a transport support 22 of a microplate reader 23. It is further preferable that the support surface 26 comprises retaining webs 28 which are arranged on the corners of the reading opening 27 and which are configured for engagement in respective retaining openings 29 in the inner wall 6 of the frame 4 of the incubation cassette 1 or the integration frame 4. Despite said secure fit, which is important and indispensable especially during the displacement of the transport support 22 into and out of the microplate reader and during the scanning of the wells in the microplate reader, the entire incubation cassette 1 with the microplate 3 and the cover 12, or also only the incubation frame 4, can simply be placed in a vertical linear movement on the transport support 22 or be lifted off therefrom.

The spring bolt 30 of the transport support is used for positioning and holding a microplate 3 which is inserted into the frame 4 of the incubation cassette 1 or into the incubation frame 4, and preferably comprises an oblique contact surface 31 which is configured for impinging on a corner of a microplate 3 inserted into the frame 4 of the incubation cassette 1. Said impinging ensures that the microplate 3 is pressed against the retaining webs 28 of the transport support 22 opposite of the oblique contact surface 31 and is thus positioned precisely on the transport support 22. If therefore a microplate 3 is to be removed from a frame 4 situated on the transport support 22, the spring bolt 30 must be moved away therefrom for releasing the microplate 3. If a frame 4 or an incubation frame 4 with inserted microplate 3 is to be lifted off the transport support 22, the spring bolt 30 must also be moved away therefrom for releasing the microplate 3.

Figure 3:
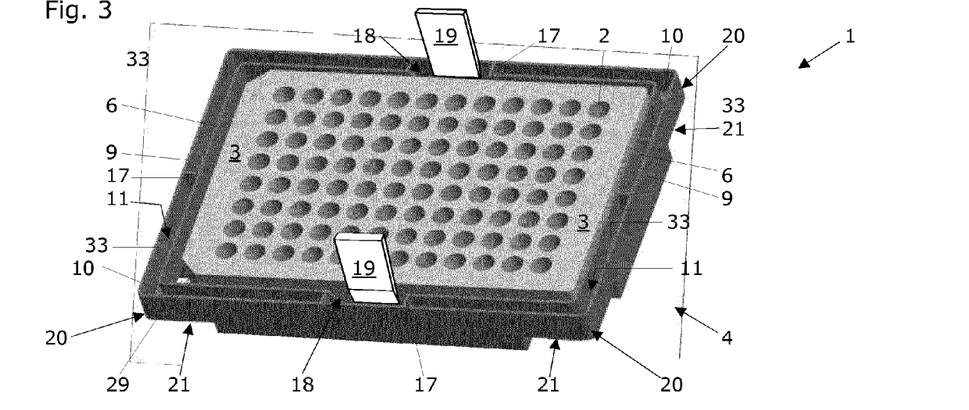
FIG. 3 shows a view of a frame of a covered incubation cassette or an incubation frame, in which a standard microplate according to ANSI_SBS 1-2-3-4-2004 standard was just inserted by means of a robot.

FIG. 3 shows a 3D view of a frame 4 of a covered incubation cassette 1 or an incubation frame 4, in which a microplate 3 is inserted by means of a robot; the removal of the microplate 3 from the frame 4 or from the incubation frame 4 would appear in precisely the same way. It is preferable for the simpler performance of such an insertion or removal that the inner wall 6 of the frame 4 comprises sections 18 (also see FIGS. 1 and 2) which are configured for the engagement of fingers 19 of a microplate handling robot (shown) or an operator (not shown) for transporting a microplate 3 (preferably a standard microplate 3 according to the ANSI_SBS 1-2-3-4-2004 standard). Apart from that, the illustration shows the same frame 4 of the incubation cassette 1 or the same incubation frame 4 as in FIG. 2, but with inserted microplate 3, so that the repeated description of the details provided with reference numerals can be avoided.

Figure 4:
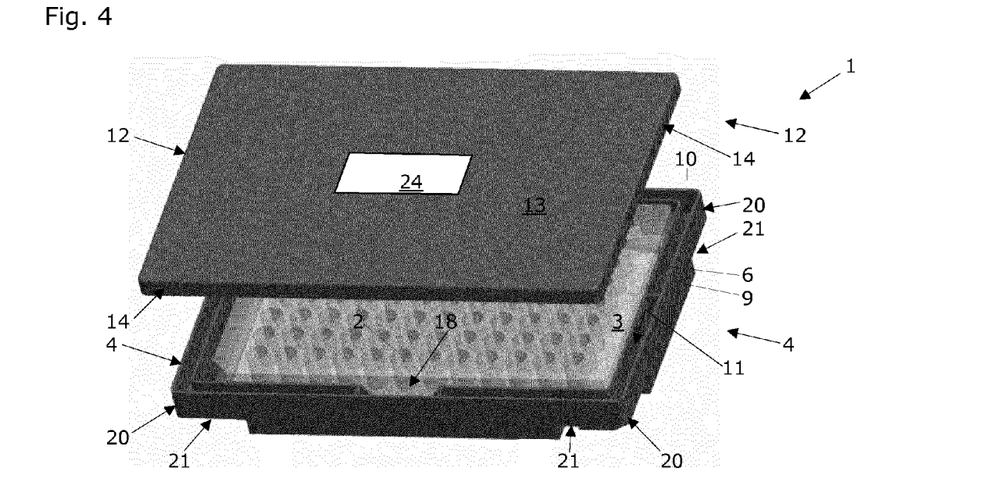
FIG. 4 shows a view of a frame of an incubation cassette with inserted standard microplate according to ANSI_SBS 1-2-3-4-2004 standard, on which a cover is just laid.

FIG. 4 shows a 3D view of a frame 4 with an incubation cassette 1 with inserted standard microplate 3, on which a cover 12 is placed. The lifting of the cover 12 from the frame 4 would appear in the same manner. The placement or removal of the cover 12 can occur outside of the housing 25 of the microplate reader 23 in a manual manner or by means of a robot. Within the housing 25, this manipulation on the cover 12 of the incubation cassette 1 preferably occurs by means of a magnetic apparatus 35 (see FIG. 2) integrated in the microplate reader 23. A preferred magnetic apparatus 35 with permanent magnets is described in the European patent application EP 13178313.6 of the current patent applicant. The illustrated cover 12 comprises a plate 13 with a magnetizable surface 24 which merely covers a portion of the plate 13. Alternatively, several such small magnetizable surfaces 24 or a single large magnetizable surface 24 can be provided, which covers the entire plate 13 at least approximately. The illustrated preferred cover 12 comprises a circumferential edge 14. Apart from that, the illustration shows the same frame 4 of the incubation cassette 1 as in FIG. 2, but with inserted microplate 3, so that the repeated description of the details provided with reference numerals can be avoided.

FIG. 5 comprises the illustrations FIGS. 5A to 5D and shows schematic vertical sections through an incubation cassette 1 covered by a cover 12 and having a microplate 3 inserted into the central first opening 5 of the frame 4, which microplate 3 rests on a support surface 7 and above the central second opening 8. The support surface 7 is connected to the inner wall 6, which on its part is connected via the intermediate bottom 7 to the outer wall 9. The outer wall 9, the intermediate bottom 10 and the inner wall 6 define the channel 11 or the liquid reservoir in which a liquid (e.g. distilled water) is filled which is adjusted to the liquid in the wells 2 of the microplate 3.

In accordance with FIG. 5A, the inner wall 6 of the frame 4 is less high than the outer wall 9, wherein—when the cover 12 is inserted—a circumferential gap 15 between the plate 13 and the upper end of the inner wall 6 connects the central first opening 5 to the channel 11 that surrounds said opening. A contiguous gas atmosphere 32 is thus produced above the reservoir or channel 11 and above the wells 2 of the microplate 3. The cover 12 comprises in this case an edge 14 that completely extends around the plate 13.

In accordance with FIG. 5B, the inner wall 6 of the frame 4 reaches up to the same height as the outer wall 9, wherein the inner wall 6 comprises depressed regions 16, so that—when the cover 12 is inserted—each depressed region 16 connects the central first opening 5 to the channel 11 that surrounds said opening. A contiguous gas atmosphere 32 is thus produced above the reservoir or channel 11 and above the wells 2 of the microplate 3. The illustration shows one of several depressed regions as a connection between the channel 11 and a first opening 5. The cover 12 comprises in this case an edge portion 34 which corresponds only to a portion of the fully circumferential edge 14 in FIG. 5A, and which is configured in such a way that it downwardly engages beyond the outer wall 9 in the region of a corner 20. For this reason, the respective notch 21 in the outer wall 9 is also shown in the region of the corner 20.

In accordance with FIG. 5C, the inner wall 6 of the frame 4 is less high than the outer wall 9, wherein—when the cover 12 is inserted—a circumferential gap 15 between the plate 13 and the upper end of the inner wall 6 connects the central first opening 5 to the channel 11 surrounding said opening. This produces a contiguous gas atmosphere 32 above the reservoir or channel 11 and above the wells 2 of the microplate 3 (also see FIG. 5A). The cover 12 is arranged in this case as a simple, rimless plate 13 and rests on the outer wall 9. In order to facilitate correct placement of the cover 12 and to prevent slippage of a placed cover 12 on the frame 4, said cover 12 comprises centering pins 40 on its bottom side. Said centering pins 40 can consist of the same material as the cover 12 and can be injections molded together with the cover or can be glued or welded onto the cover 12. Furthermore, the cover 12 can comprise a circumferential seal on its bottom side or the outer wall at its highest position (both are not shown), which additionally improves the sealing of the incubation cassette 1.

In accordance with FIG. 5D, the inner wall 6 of the frame 4 reaches up to virtually the same height as the outer wall 9, wherein the inner wall 6 comprises depressed regions 16, so that—when the cover 12 is inserted—each depressed region 16 connects the central first opening 5 to the channel 11 which surrounds said opening. This produces a contiguous gas atmosphere 32 above the reservoir or channel 11 and above the wells 2 of the microplate 3. The illustration shows two of several depressed regions 16 as a connection between the channel 11 and a first opening 5 (also see FIG. 5B). The outer wall 9 is enlarged in its upper region and comprises a shoulder 41 which is impinged by the cover 12. The cover 12 is configured in this case as a simple plate and is prevented from slipping by and upwardly protruding portion 42 of the outer wall 9. The cover 12 can comprise a circumferential seal on its bottom side, or the shoulder 41 and/or the inner surface of the upwardly protruding portion 42 of the outer wall 9 can comprise a circumferential seal (both are not shown), which seal additionally improves the sealing of the incubation cassette 1.

The incubation cassettes 1 in accordance with the invention, which is equipped with an inserted 96-well flat-bottom microplate 3 according to the ANSI_SBS 1-2-3-4-2004 standard, are placed on the transport support 22 of a microplate reader 23. The wells 2 of said microplates 3 are respectively provided with a hydrous liquid sample with a volume of 200 μL each. In the channel 11 of the incubation cassette 1, which surrounds the central first opening 5, a volume of approximately 10 mL of distilled water, which approximately corresponds to the total volume of the liquid samples in the wells 2 of the microplates 3, is filled or distributed among the channel sections 33.

It was observed in an incubation cassette 1 in which the channel 11 was not subdivided by the webs 17 that water escapes from the channel 11 by spilling already during routine displacement of the transport support 22 in the microplate reader 23. It was observed in the case of an incubation cassette 1, in which the channel 11 is subdivided in accordance with FIG. 2 by webs 17 into channel sections 33, that it is less susceptible to such spilling of the water. However, there is a substantially higher likelihood of the spilling of liquid from the channel 11 or from the channel sections 33 during agitation of a microplate 3 situated in the incubation cassette 1, i.e. during the agitation of the liquid samples in the wells 2 of said microplate on an agitator. Spilling of the liquid samples from the wells 2 of the microplates 3 was not observed at any time.

Many measures were tried to prevent such spilling from the channel 11:

1. The channel 11 or the channel sections 33 were lined with a sponge-like material (e.g. domestic sponge, medical fleece). This measure is not preferred because said sponge-like material requires a specific volume itself on the one hand and thus the filling volume decreases in this manner. On the other hand, said sponge-like material can easily drop out of the channel 11 or from the channel sections 33 and can be lost. The fixing (gluing) of the sponge-like material in the liquid reservoir, i.e. in the channel 11 or in the channel sections 33 is very complex and can additionally reduce the useful filling volume.

2. Providing a plurality of webs 17 and thus a subdivision of the channel 11 into increasingly smaller channel sections 33 can considerably reduce spillage. Such an installation of numerous transverse webs as "wave breakers" also does not represent a preferred solution because the distribution of the liquid volume in the channel 11 becomes more complex because the water will no longer automatically distribute in the reservoir in the case of high webs. The achievable effect is insufficient in the case of an alternative with webs of such a low height that the water will still distribute sufficiently in the reservoir.

3. Increasing the viscosity of the liquid in the reservoir with at least approximately similar evaporation behavior appears to be the most promising solution. Gel formation by means of gelatin, agarose gel, methyl cellulose etc or the admixture of liquids of high viscosity such as glycerin, glycol etc, can be considered for example.

A number of requirements need to be considered for increasing the viscosity of the liquid in the reservoir:

The gel-forming agent must not be more than slightly hygroscopic in order to ensure the evaporation of the reservoir liquid that is "sacrificed" (glycerin or glycol are unsuitable for this purpose);

The gel must be easy to produce and without any major effort (gelatin and agarose gels which need to be cooked first are unsuitable in this case);

Reservoirs which are filled with a gel and are dried-up or surface-dried during use in the microplate reader must reach their swollen state again during refilling (e.g. by means of an injector) within a short period of time (unsuitable are gelatin, agarose and methyl cellulose);

The gel-forming material must be unsuitable as a culture medium for microorganisms, because cell cultures in microplates are susceptible to contamination by fungi or bacteria from the ambient environment (unsuitable are gelatin and agarose gels);

The costs for the gel-forming agent must be as low as possible;

The gel-forming agent must have the lowest possible weight share.

A material was found which is ideal in all respects for use as a gel-forming agent in the channel 11 or in the channel sections 33, namely polyacrylic acid-sodium salt (e.g. from Sigma-Aldrich, order No. 436364):

Polyacrylic acid swells within 3 minutes to 200 times its volume, wherein 6 g/L of polyacrylate/water produce a useful gel for example;

The water from said polyacrylate gel evaporates virtually with the same speed as pure water: a sample of distilled water lost approximately 68% of the initial volume during storage of 7 hours in a heating cabinet at 50° C., whereas a mixture (1.6% by weight of polyacrylic acid water) lost approximately 60% of the initial volume under the same conditions; the water from the polyacrylate gel thus evaporates only approximately 8% slower than pure water;

Once completely dried, the polyacrylate gel rapidly swells again with renewed addition of water;

The polyacrylic acid gel is detested by all small living beings (a polyacrylate gel was left in the open for three months without noticing any contamination by microorganisms);

The polyacrylic acid gel does not present any health risk and is used in the pharmaceutical industry (e.g. EP 0 744 951 B1) for producing hygiene articles with increased absorption capability for body fluids (cf. EP 1 137 678 B1) and in gardening (cf. WO 98/49252 A1);

The required quantity of polyacrylic acid per incubation cassette 1 merely costs a fraction of a eurocent and raises the price for the production of an integration cassette 1 only insubstantially;

Ideally, polyacrylate grains are fixed with a low quantity water-soluble adhesive (e.g. polyvinyl alcohol, polyvinyl acetate, polyvinyl pyrrolidone) in the reservoir of the incubation cassette 1, so that the user only needs to fill water as usual.

Prior to the filling of the liquid into the channel 11 or into the channel sections 33 of an incubation cassette 1 placed on the transport support 22, a cover 12 presented in FIG. 1 can be lifted in a manual manner or by means of a robot of a laboratory workstation (not shown) from the frame 4 of the incubation cassette 1 by means of a magnetic apparatus 35 (shown in FIG. 2 with the dashed line) integrated in the housing 25 of the microplate reader 23. In addition or alternatively, a cover 12 which is equipped in such a way and comprises a magnetizable surface 24 can be placed in a manual manner or by means of a robot of a laboratory workstation (not shown) on the frame 4 of the incubation cassette 1 by means of a magnetic apparatus 35 (shown in FIG. 2 with the dashed line) integrated in the housing 25 of the microplate reader 23 after the filling of the liquid into the channel 11 or into the channel sections 33 of an incubation cassette 1 placed on the transport support 22. The microplate reader 23 preferably comprises a magnetic apparatus 35 integrated in the housing 25 for lifting and depositing the cover 12 of an integration cassette 1 placed on the transport support 22.

The channel 11 or the channel sections 33 of a frame or an incubation frame 4 are preferably filled at least partly with a liquid (e.g. with distilled water), wherein a hand pipette, a pipette of a laboratory workstation or an injector of the microplate reader 23 is used for filling the liquid into the channel 11 or into the channel sections 33. This enables or supports the use of the incubation cassette 1 or incubation frame 4 in accordance with the invention for reducing liquid evaporation from the wells 2 of microplates 3 in a microplate reader 23. If microplates 3 are to be used according to a standard other than ANSI_SBS 1-2-3-4-2004, the dimensions of the incubation cassette 1 or incubation frame 4 can be adjusted accordingly.

Figure 6:
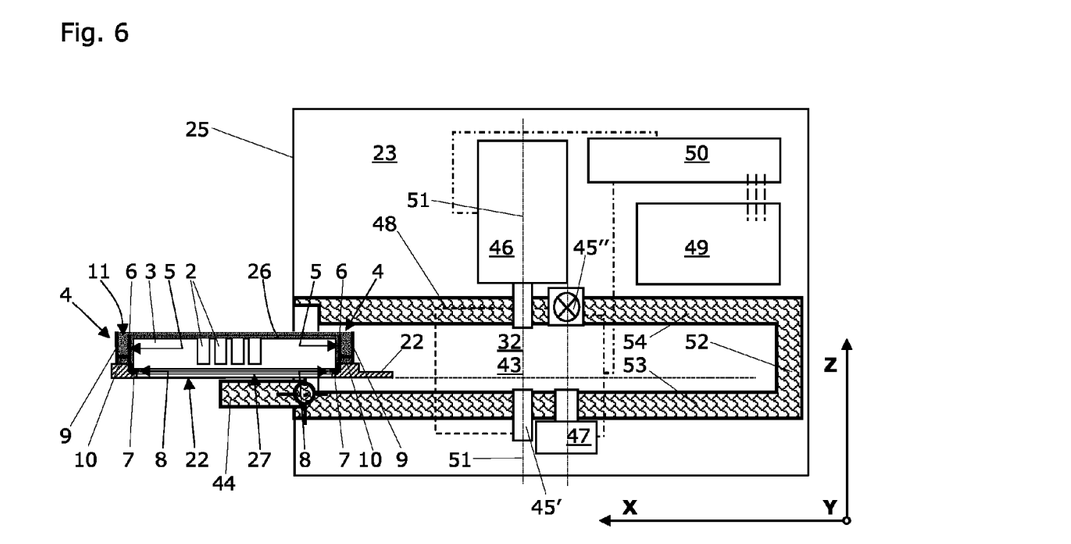
FIG. 6 shows a vertical sectional view through a microplate reader with small measuring space volume, in which a transport support with incubation frame and microplate is retracted or from which a transport support with incubation frame and microplate is extended.

FIG. 6 shows a vertical sectional view through a microplate reader 23 with minimized measuring space volume when drawing a microplate 3 into the measuring space 43 which is preferably arranged as a chamber that can be sealed in a light-tight manner. Said microplate reader 23 comprises a transport support 22 for accommodating at least one microplate or a standard microplate 3 with wells 2 containing biological structures, of which only four are shown.

In connection with the present invention, the term "biological structures" comprises tissue parts such as of humans, animals or plants; cell cultures or parts thereof; individual cells; cell organelles; macromolecules such as nucleic acids or proteins as well as individual molecules such as nucleotides, amino acids, hormones and metabolites.

Said transport support 22 is preferably configured to be extensible to such an extent from the measuring space 43 of the microplate reader 23 that at least one frame 4 of an incubation cassette 1 or an incubation frame 4 and/or a microplate 3 can be inserted into said transport support 22 or lifted therefrom manually or by means of a microplate handling robot (both are not shown). The transport support 22 is already partly retracted in this case because a microplate 3 and the incubation frame 4 surrounding said microplate are just inserted into the microplate reader 23. During the insertion or ejection of a microplate 3 and the incubation frame 4 surrounding said microplate, a flap 44 is preferably open, which in the closed state preferably seals the measuring space 43 in a light-tight manner, so that no light that would influence the examinations can reach the measuring space 43 from the ambient environment. In addition to receiving at least one microplate 3 and an incubation frame 4 surrounding said microplate, said transport support 22 is used for positioning the microplate 3 with the wells 2 containing the biological structures (e.g. metabolites, macromolecules, cells or cell cultures) against the action sources 45', 45" and against the measuring devices 46, 47 of the microplate reader 23, or against the optical axes 51 of the measuring devices 46, 47. The illustrated microplate reader 23 further comprises at least one action source 45', 45" for producing an interaction between at least one of said sources 45', 45" and biological structures in specific wells 2 of the microplate 3 and for effecting or generating a measurable signal. Such signals comprise fluorescence emission, luminescence emission, reflected light and transmitted light.

In this embodiment, a first light source is used as an action source 45' for exciting fluorescence in or on biological structures in wells 2 of said microplate 3 and a first measuring device 46 (provided here in form of a photomultiplier tube) is used for the so-called "top reading" of fluorescence emitted by the samples with respect to an optical axis 51. Alternatively, both the excitation from above and also the detection of fluorescence can occur by means of top reading. If on the other hand luminescence of samples is to be detected in top reading, one action source can even be omitted. A second light source is used in this case as an action source 45" for illuminating biological structures in wells 2 of said microplate 3 and a second measuring device 47 (provided here in form of a digital camera) is used for the so-called "bottom reading" of the absorbance of the samples with respect to an optical axis 51.

Such light sources are selected for example from a group which comprises arc lamps, flash lamps, incandescent lamps (such as halogen lamps), lasers, laser diodes and light-emitting diodes (LEDs). The respective wavelengths for exciting fluorescence and the respective fluorophores and their emission characteristics are also known to the person skilled in the art and are selected according to the application. The person skilled in the art is also familiar with the non-invasive radiographic examination of cells or cell cultures for detecting the absorbance and the light sources used for this purpose. Measuring devices 46, 47 for detecting at least one integral signal which was produced or generated by the action source(s) 45', 45" in or on biological structures in the specific wells 2 of the microplate 3 are preferably selected from a group which comprises photomultipliers, photodiodes, photodiode arrays and avalanche diodes. The measuring devices 46, 47 and the light sources 45', 45" or their optical input and/or output are preferably coupled via optical waveguides 48 such as optical fibers or optical fiber bundles.

The measuring space 43 illustrated in FIG. 6 is arranged in a light-tight way and is preferably minimized with respect to its size in such a way that at least one microplate 3 and one incubation frame 4 surrounding said microplate can be moved therein in such a way that all wells 2 of the microplate 3 containing the biological structures can be positioned against the action sources 45', 45" and the measuring devices 46, 47 of the microplate reader 23 or against the optical axes 51 of the microplate reader 23. The minimized volume of the measuring space 43 promotes maintaining a humid gas atmosphere 32 in its interior by the evaporation of the liquid from the incubation frame 4, which is used in this case without the cover 12. Said measuring space 43 preferably comprises a virtually gas-tight enclosure, which comprises walls 52, bottom 53, top 54 and flap 44 and which is configured for maintaining the humid gas atmosphere 32.

The microplate reader 23 in accordance with the invention further comprises a housing 25 and an internal or integrated processor 49, or it is configured to be connectable to an external processor (not shown). Such a processor 49 can thus be a microprocessor integrated in the electronic control of the microplate reader 23, or it can be a provided personal computer.

The same reference numerals in the drawings designate the same or at least similar features, even though they are not explained in detail in all cases.

| List of reference numerals | |
|---|---|
| 1 | Incubation cassette |
| 2 | Well |
| 3 | Microplate, standard microplate |
| 4 | Frame, incubation frame |
| 5 | Central first opening, first opening |
| 6 | Inner wall |
| 7 | Support surface of 4 |
| 8 | Central second opening, second opening |
| 9 | Outer wall |
| 10 | Intermediate bottom |
| 11 | Channel, reservoir |
| 12 | Cover |
| 13 | Plate of 12 |
| 14 | Circumferential edge of 12 |
| 15 | Circumferential gap |
| 16 | Depressed region |
| 17 | Web in 11 |
| 18 | Section |
| 19 | Finger |
| 20 | Corner of 4 |
| 21 | Notch |
| 22 | Transport support |
| 23 | Microplate reader |

-continued

| | List of reference numerals |
|---|---|
| 24 | Magnetizable surface |
| 25 | Housing |
| 26 | Support surface |
| 27 | Reading opening |
| 28 | Retaining webs |
| 29 | Retaining opening |
| 30 | Spring bolt |
| 31 | Oblique contact surface |
| 32 | Gas atmosphere |
| 33 | Channel sections |
| 34 | Edge portions of 12 |
| 35 | Magnetic apparatus |
| 40 | Centering pins |
| 41 | Shoulder |
| 42 | Upwardly protruding portion of 9 |
| 43 | Measuring space |
| 44 | Flap |
| 45' | First action source |
| 45" | Second action source |
| 46 | First measuring device |
| 47 | Second measuring device |
| 48 | Optical waveguide |
| 49 | Processor |
| 50 | Controller |
| 51 | Optical axis |
| 52 | Measuring space wall |
| 53 | Measuring space bottom |
| 54 | Measuring space ceiling |

The invention claimed is:

1. A microplate reader (23), at least comprising:
   a) a measuring space (43);
   b) an action source (45') which is configured for producing an interaction with biological structures in wells (2) of a microplate (3) and for effecting or generating a measurable signal;
   c) a measuring device (46) which is configured for detecting a signal emitted by the biological structures in wells (2) of a microplate (3), or which was effected or generated by the action source (45') in or on biological structures in wells (2) of a microplate (3), wherein the measuring device (46) defines an optical axis (51);
   d) a transport support (22) which can be extended at least partly out of the measuring space (23) and which is configured for positioning wells (2) of a microplate (3) in relation to the optical axis (51) of the measuring device (46) of the microplate reader (23), in that the transport support (22) is configured to be movable in at least one direction within the measuring space (43), and
   e) a controller (50) which is formed for controlling the action source (45') of the measuring device (46) and the movements of the transport support (22) of the microplate reader (23);
wherein the microplate reader (23) comprises an incubation apparatus for reducing liquid evaporation from wells (2) of a microplate (3), wherein:
   (i) the incubation apparatus comprises a frame (4) for accommodating a microplate (3) with wells (2) having well bottoms;
   (ii) the frame (4) comprises a first opening (5) surrounded by an inner wall (6), the dimensions of which are configured for inserting a microplate (3), and
   (iii) the frame (4) comprises an outer wall (9) which extends substantially parallel to the inner wall (6) and which is connected to the inner wall (6) via an intermediate bottom (10), so that a channel (11) surrounding the first opening (5) is formed by the two walls (6, 9) and the intermediate bottom (10) for accommodating a liquid adjusted to the content of the microplate wells (2);
that the incubation apparatus comprises a support surface (7) with a second opening (8), wherein said that support surface (7) is arranged on the inner wall (6) for supporting an inserted microplate (3), and wherein as a result of the second opening (8) all of the bottoms of the wells (2) of a microplate (3) inserted into the incubation apparatus are freely accessible by the second opening (8);
the transport support (22) of the microplate reader (23) comprises at least one support surface (26) with a reading opening (27) which is configured for placing or lifting the incubation apparatus and/or a microplate (3),
and that the reading opening (27) of the transport support (22) is adjusted with respect to its size and position to the second opening (8) of the frame (4) of the incubation apparatus in such a way that all bottoms of the wells (2) of a microplate (3) inserted into the incubation apparatus are freely accessible by the reading opening (27).

2. A microplate reader (23) according to claim 1, characterized in that the support surface (26) of the transport support (22) comprises retaining webs (28) which are arranged on the corners of the reading opening (27) and which are configured for engaging in respective retaining openings (29) in the inner wall (6) of the frame (4) of the incubation apparatus.

3. A microplate reader (23) according to claim 1, wherein the transport support (22) comprises a spring bolt (30) for positioning and holding a microplate (3) inserted into the frame (4) of the incubation apparatus.

4. A microplate reader (23) according to claim 3, characterized in that the spring bolt (30) comprises an oblique contact surface (31) which is configured for impinging a corner of a microplate (3) inserted into the frame (4) of the incubation apparatus, wherein said impinging ensures that the microplate (3) inserted into the incubation apparatus is pressed against the retaining webs (28) of the transport support (22) which are opposite of the oblique contact surface (31) and is positioned precisely on the transport support (22).

5. A microplate reader (23) according to claim 1, characterized in that the microplate reader (23) comprises a housing (25) with an integrated magnetic apparatus (35) which is configured for lifting and placing the cover (12) of an incubation cassette (1) placed on the transport support (22).

6. A microplate reader (23) according to claim 1, characterized in that the measuring space (43) has a minimized volume and comprises a virtually gas-tight enclosure (44, 52, 53, 54) which is configured for maintaining a humid gas atmosphere (32) which is produced by the evaporation of liquid from the incubation frame (4).

7. An incubation apparatus for use in a microplate reader (23) according to claim 1, characterized in that
   (i) the incubation apparatus comprises a frame (4) for accommodating a microplate (3) with wells (2) having well bottoms;
   (ii) the frame (4) comprises a first opening (5) surrounded by an inner wall (6), the dimensions of which are configured for inserting a microplate (3), and
   (iii) the frame (4) comprises an outer wall (9) which extends substantially parallel to the inner wall (6) and which is connected to the inner wall (6) via an intermediate bottom (10), so that a channel (11) surrounding the first opening (5) is formed by the two walls (6, 9)

and the intermediate bottom (10) for accommodating a liquid adjusted to the content of the microplate wells (2);

wherein the incubation apparatus comprises a support surface (7) with a second opening (8), wherein said that support surface (7) is arranged on the inner wall (6) for supporting an inserted microplate (3), and wherein as a result of the second opening (8) all of the bottoms of the wells (2) of a microplate (3) inserted into the incubation apparatus are freely accessible by the second opening (8), and wherein the incubation apparatus is configured as an incubation cassette (1) with a frame (4) and a cover (12), or as a cover-free incubation frame (4).

8. An incubation apparatus according to claim 7, characterized in that the incubation apparatus is configured as an incubation cassette (1) with a frame (4) and a cover (12), wherein the cover (12) for covering the frame (4) of the incubation cassette (1) comprises a substantially flat plate (13) and, integrally formed on said plate (13), a downwardly protruding and circumferential edge (14) or several downwardly protruding edge portions (34), wherein the cover (12) is configured for placement on the frame (4) in such a way that the plate (13) rests on an upper end of the outer wall (9) and said edge (14) or the edge portions (34) of the cover (12) engage downwardly beyond the outer wall (9) of the frame (4).

9. An incubation apparatus according to claim 7, characterized in that the incubation apparatus is configured as an incubation cassette (1) with a frame (4) and a cover (12), wherein the cover (12) for covering the frame (4) of the incubation cassette (1) is configured as a substantially flat plate (13) with or without centering pins (40).

10. An incubation apparatus according to claim 8, characterized in that the inner wall (6) of the frame (4) reaches up to a lower height than the outer wall (9), so that when the cover (12) is placed a circumferential gap (15) connects the central first opening (5) to the channel or reservoir (11) surrounding said opening.

11. An incubation apparatus according to claim 8, characterized in that the inner wall (6) of the frame (4) reaches up to the same height as the outer wall (9), and that the inner wall (6) comprises depressed regions (16), so that when the cover (12) is placed each depressed region (16) connects the central first opening (5) to the channel or reservoir (11) surrounding said opening.

12. An incubation apparatus according to claim 8, characterized in that the cover (12) comprises an at least partly metalized, magnetizable surface (24), wherein said magnetizable surface (24) is selected from a group which comprises a self-adhesive metal foil, an extrusion-coated metal plate and a glued metal plate, and wherein the metal comprises iron, nickel and their alloys.

13. An incubation apparatus according to claim 7, characterized in that the inner wall (6) of the frame (4) is connected via substantially perpendicular webs (17) to the outer wall (9) of the frame (4), by means of which the channel (11) is subdivided into a number of channel sections (33).

14. An incubation apparatus according to claim 7, characterized in that the inner wall (6) of the frame (4) comprises sections (18) which are configured for the engagement of fingers (19) of a microplate handling robot or an operator for transporting a microplate (3).

15. An incubation apparatus according to claim 7, characterized in that the channel (11) surrounding the first central opening (5) comprises a water-binding material, which at temperatures of at least 35° C., preferably at least 25° C., emits water vapor to a gas atmosphere (32) provided above the wells (2) of the microplate (3).

16. An incubation apparatus according to claim 15, characterized in that the hygroscopic material is a swellable polyacrylic acid salt.

17. An incubation apparatus according to claim 7, characterized in that said incubation cassette (1) or said incubation frame (4) is configured for accommodating a standard microplate (3) according to the ANSI_SBS 1-2-3-4-2004 standard.

18. An incubation apparatus according to claim 7, wherein the outer wall (9) comprises notches (21) on all corners (20) of the frame (4), which notches are configured for placing the frame (4), with or without a microplate (3) inserted into said frame (4), onto a transport support (22) of a microplate reader (23).

* * * * *